United States Patent
Kreber

(10) Patent No.: US 9,561,297 B2
(45) Date of Patent: Feb. 7, 2017

(54) STERILIZATION METHOD

(71) Applicant: Fresenius Medical Care Deutschland GmbH, Bad Homburg (DE)

(72) Inventor: Stefan Kreber, Saarbruecken (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 614 days.

(21) Appl. No.: 14/043,041

(22) Filed: Oct. 1, 2013

(65) Prior Publication Data

US 2014/0105786 A1 Apr. 17, 2014

Related U.S. Application Data

(60) Provisional application No. 61/712,485, filed on Oct. 11, 2012.

(30) Foreign Application Priority Data

Oct. 11, 2012 (DE) .................. 10 2012 019 937

(51) Int. Cl.
*A61L 2/20* (2006.01)
*A61L 2/07* (2006.01)

(52) U.S. Cl.
CPC .. *A61L 2/20* (2013.01); *A61L 2/07* (2013.01); *A61L 2/202* (2013.01); *A61L 2/204* (2013.01); *A61L 2/206* (2013.01); *A61L 2/208* (2013.01)

(58) Field of Classification Search
CPC ................. A61L 2/07; A61L 2202/122; A61L 2202/181; A61L 2/20; A61L 2/202; A61L 2/204;A61L 2/206; A61L 2/208; B04B 5/0442
See application file for complete search history.

(56) References Cited

U.S. PATENT DOCUMENTS

| 3,468,471 | A | * | 9/1969 | Linder | ...................... | A61L 2/26 |
| | | | | | | 174/110 N |
| 5,842,326 | A | | 12/1998 | Wolf | | |
| 2003/0007914 | A1 | * | 1/2003 | Ongaro | ..................... | A61L 2/07 |
| | | | | | | 422/292 |

(Continued)

FOREIGN PATENT DOCUMENTS

| AU | 526378 | 1/1983 |
| CH | 235 388 | 11/1944 |

(Continued)

OTHER PUBLICATIONS

Block "Disinfection, Sterilization, and Preservation." Dec. 31, 2001, pp. 706-710, and 761, XP002717908.

*Primary Examiner* — Timothy Cleveland
(74) *Attorney, Agent, or Firm* — Jacobson Holman, PLLC.

(57) ABSTRACT

The invention relates to a fractional vacuum sterilization method for objects such as blood tubing systems or cassette systems, which are sterilized in outer packagings. The spatial extent of the outer packaging during the evacuation step is minimized here by inserting a packing into the sterilization chamber and thereby achieving an efficient gas exchange through the gas-permeable outer packaging. The number of vacuum-pressure cycles required to establish a saturated sterilization medium atmosphere in the outer packaging and in the object to be sterilized is thereby reduced.

10 Claims, 3 Drawing Sheets

(56) References Cited

U.S. PATENT DOCUMENTS

| | | |
|---|---|---|
| 2004/0091389 A1 | 5/2004 | Malkin et al. |
| 2004/0127840 A1* | 7/2004 | Gara .................... B04B 5/0442 604/4.01 |
| 2009/0238937 A1 | 9/2009 | Yamazaki et al. |

FOREIGN PATENT DOCUMENTS

| | | |
|---|---|---|
| DE | 1116349 | 11/1961 |
| DE | 10114758 | 9/2002 |
| EP | 1484069 | 12/2004 |
| WO | WO 95/00180 | 1/1995 |
| WO | WO 01/76646 | 10/2001 |
| WO | WO 2011119357 A1 * | 9/2011 ............... A61L 2/07 |

* cited by examiner

STERILIZATION METHOD

SUMMARY/ABSTRACT

The invention relates to the field of sterilization using the fractional vacuum steam method.

STATE OF THE ART

The fractional vacuum steam method is a disinfection method that is recognized by the Robert Koch Institute and is used mostly for difficult-to-evacuate products, e.g., tubing systems or cassette systems. Such a method is described, for example, in Wallhäußer, Praxis der Sterilisation, Desinfektion, Antiseptik and Konservierung [Practice of Sterilization, Disinfection, Antiseptics and Conservation], and also in DE 101 14 758 A1.

STATEMENT OF PROBLEM

Disposable items for medical applications must often be sterilized post production. The fractional vacuum steam method is used most widely in the case of plastic products with air-filled cavities, e.g., the aforementioned tubing systems or cassette systems, which are not suitable for dry heat sterilization.

In this method, the products to be sterilized are inserted into a vacuum-tight sealing chamber. Then the air in the chamber and in the products to be sterilized is replaced by the sterilization medium by repeated evacuation of the chamber in alternation with inflow of sterilization medium. If the entire atmosphere in the sterilization chamber has been saturated with sterilization medium, there is an incubation phase with the sterilization medium until achieving the desired sterilization. After this incubation phase, the sterilization medium is removed by switching between vacuum phases and the introduction of sterile gas. In the last step, the sterilization chamber is flooded with sterile gas, and then the chamber can be opened and the sterilization item(s) can be removed.

To ensure the sterility of the products for shipping and storage, the sterilization is usually performed in bag-shaped outer packaging consisting of a mostly gas-impermeable transparent film on one side and a gas-permeable paper on the other side, so that the sterilization medium can pass through the packaging to the sterilization item(s).

The products to be sterilized, e.g., tubing systems, are introduced into the outer packaging bags under atmospheric pressure, and this bag is then sealed by gluing or welding. A gas exchange is possible only through the gas-permeable paper. However, the flow resistance through the paper is significant for the process described here and has an influence on the number of steam cycles to be performed to achieve an adequate replacement of air by sterilization medium.

If a vacuum is then applied to the sterilization chamber, the gas in the sterilization item(s) first escapes into the outer packaging bag. The bag inflates to the maximum filling volume. Only when this has been achieved is there an exchange of gas through the gas-permeable part of the outer packaging. The inflated bag is compressed in the switch to the inflow phase. The air in the bag is then forced back into the sterilization item(s). This results in an inefficient exchange due to the air moving back and forth between the inside volume of the sterilization item(s) and the filling volume of the packaging bag, which is why a greater number of evacuation cycles is needed before the incubation phase. The same is also true for the evacuation cycles, which are then performed after incubation to remove the sterilization medium.

Another negative aspect is that the packaging bag is inflated vertically, which results in a reduction in the size of the cross section. This may lead to increased contact of the sterilization item(s) with the packaging film, depending on the geometric dimensions of the sterilization item(s), so that sticking may occur at the elevated temperatures at which sterilization takes place.

It is the object of the present invention to make available an improved sterilization method. Such a sterilization method should achieve a more efficient gas exchange in the outer packaging, for example.

In addition, sticking between the transparent film and the outer packaging and the contents of the outer packaging should be prevented.

In the teaching according to the present invention, this object is achieved by a sterilization method according to claim 1, a sterilization device according to claim 10 and the use of a packing according to claim 15. Special embodiments are the subject of the dependent claims.

SUMMARY OF THE INVENTION

With the sterilization method according to the invention, the object to be sterilized, hereinafter to be referred to as "the sterilization item," is inserted into an evacuable sterilization chamber. Then a packing is inserted. The sequence here is irrelevant, i.e., the packing may also be inserted first, but the two may also be introduced into the sterilization chamber at the same time. Next the sterilization chamber is evacuated, preferably setting a pressure of less than 110 mbar. Once the desired vacuum has been reached, a sterilization medium is introduced into the sterilization chamber, causing the pressure in the sterilization chamber to rise again. A pressure above 2 bar is preferably established. Evacuation of the sterilization chamber and introduction of sterilization medium are repeated until air initially present in the sterilization chamber and in the objects to be sterilized is replaced by an almost saturated sterilization medium atmosphere. The term "almost" here means that the degree of saturation is sufficient to ensure sterilization and this should also include a saturated sterilization medium atmosphere.

Then there is an incubation phase with the sterilization medium, i.e., the sterilization medium is left in the sterilization chamber for a predetermined period of time until a predetermined level of disinfection has been achieved.

The sterilization chamber is then evacuated again and then flooded with a sterile gas, e.g., sterile air.

These two steps are repeated until the sterilization medium has been removed from the sterilization chamber and the sterilization item(s). The sterilization chamber is then opened and the sterilization item(s) is (are) removed from the chamber.

All conventional gaseous sterilization media, e.g., hot steam, hydrogen peroxide, ozone or ethylene oxide may be used in the method according to the invention.

The replacement of air by the sterilization medium can be accelerated by the use of a packing which replaces some of the ambient air in the sterilization chamber due to its volume. It is especially advantageous here if the packing is a flexible closed gas-inflated hollow body, which may preferably be a closed plastic bag, e.g., a plastic bag that is welded on all four sides, contains a small amount of gas but is not completely filled. If a vacuum is then formed by pumping the air out of the sterilization chamber, the bag will expand to its maximum achievable volume. The space to be evacuated is thus reduced and the evacuation step may be accelerated.

An additional positive effect can be achieved with packaged sterilization item(s). In a preferred embodiment, the sterilization item(s) may be situated in a gas-permeable outer packaging. The gas-permeable outer packaging may consist of a gas-permeable layer, e.g., a paper layer on one side and a largely gas-tight transparent film on a second side.

In a preferred embodiment, the gas-permeable outer packaging may be flexible.

In the evacuation step, air may escape from the packaging through the gas-permeable packaging, and conversely, in loading the sterilization chamber with sterilization medium, the latter may penetrate into the packaging.

With the known vacuum sterilization methods, the outer packaging bag, which was filled and sealed at ambient pressure, expands to its maximum volume at first due to the drop in pressure during the evacuation step. Only then does the air present in the packaging and in the sterilization item(s) pass through the packaging and into the sterilization chamber. At the end of the evacuation step, a quantity of air corresponding to the maximum volume of the packaging remains in the packaging. Then in the next step, namely the introduction of the sterilization medium and the associated increase in pressure, the air is compressed and forced back into the sterilization item(s), which may comprise cavities. Then with an increase in pressure, the sterilization medium in the packaging is also transferred into the cavities in the sterilization item(s).

Next the space for expansion of the outer packaging bag in the evacuation step is reduced due to the packing in the sterilization chamber. The outer packaging then can no longer expand to the maximum volume, so there is a transfer of air out of the packaging and into the sterilization chamber at an earlier time. Since the packaging is compressed, less air that can be forced back into the sterilization item(s) is present in the packaging at the end of the evacuation step. A flexible packing has proven to be especially advantageous here because it will adapt to the shape of the object and may thus form the most efficient possible restriction of space. For example, a flexible bag may push into the depressions in the packaging of a tubing system.

The packing may preferably be designed so that it does not expand until the evacuation step. It is much smaller under ambient conditions and thus can be inserted together with the sterilization item(s) into the sterilization chamber and can also be removed again with no problem.

The inserts, e.g., the insertion plates or baskets to hold the sterilization item(s) in the sterilization chamber should be arranged so that the outer packaging with the sterilization item(s) is compressed due to the expansion of the packing in the evacuation step, and the extent of the outer packaging is minimized.

The packing should preferably be essentially at least as large as the outer packaging in its base area. In an especially preferred embodiment the base area of the packing corresponds approximately to the base area of the inserts in the sterilization chamber which serve to receive the sterilization item(s).

In an especially preferred embodiment, an outer packaging bag is first inserted into the sterilization chamber and then a packing is inserted and next again an outer packaging bag so that the packing is situated between the two outer packaging bags. The packing arranged between the two outer packaging bags can then prevent the expansion of the two outer packaging bags during the evacuation step.

The method according to the invention may preferably be used in sterilization of objects having air-filled cavities that are open to the environment, with tubing systems or cassette systems being especially preferred.

With the method according to the invention, all conventional sterilization devices in which a vacuum can be generated in the sterilization chamber may be used.

The invention also relates to a sterilization device having an evacuable sterilization chamber, means for generating a vacuum and means for providing//supplying a sterilization medium.

The sterilization device is characterized in that the sterilization chamber has a packing.

In a preferred embodiment the packing may comprise a flexible gas-containing closed hollow body, for example a closed plastic bag.

The sterilization device may additionally have means for creating a sterilization medium; for example, said means may create ozone.

The sterilization device may additionally have means for supplying the sterilization medium into the sterilization chamber. Said means may be identical to the means for generating the vacuum.

The means for generating the vacuum may be a conventional vacuum pump, for example, a rotary disk pump or a diaphragm pump.

In addition, the sterilization device may have a control or regulating unit so that the performance of the method according to the invention can be controlled and/or regulated and/or monitored, preferably semiautomatically and/or fully automatically controllable and/or regulable and/or monitorable.

Another aspect of the present invention is the use of a packing, preferably a flexible gas-containing plastic bag in a sterilization device as described above or in a method of fractional vacuum sterilization.

Exemplary embodiments of the invention are shown in the figures.

DESCRIPTION

In the method according to the invention, sterilization item(s) and the packing are introduced into the sterilization chamber in the first step 100. The sterilization chamber is then hermetically sealed in a step 101 and then is evacuated in a step 102. Once the desired vacuum has been achieved, the introduction of the sterilization medium 103 begins. The evacuation 102 and the introduction of the sterilization medium 103 are repeated until an almost saturated atmosphere of the sterilization medium has been achieved in the sterilization chamber. Then the sterilization item(s) is incubated 104 until reaching the desired degree of disinfection. The sterilization chamber is then evacuated again in a step 105 and is next aerated with a sterile gas in a step 106. The steps 105 and 106 are repeated until the sterilization medium has been removed almost completely from the sterilization chamber. After a last aeration 106, the sterilization chamber may be opened and the sterilization item(s) may be removed.

Figure 1:
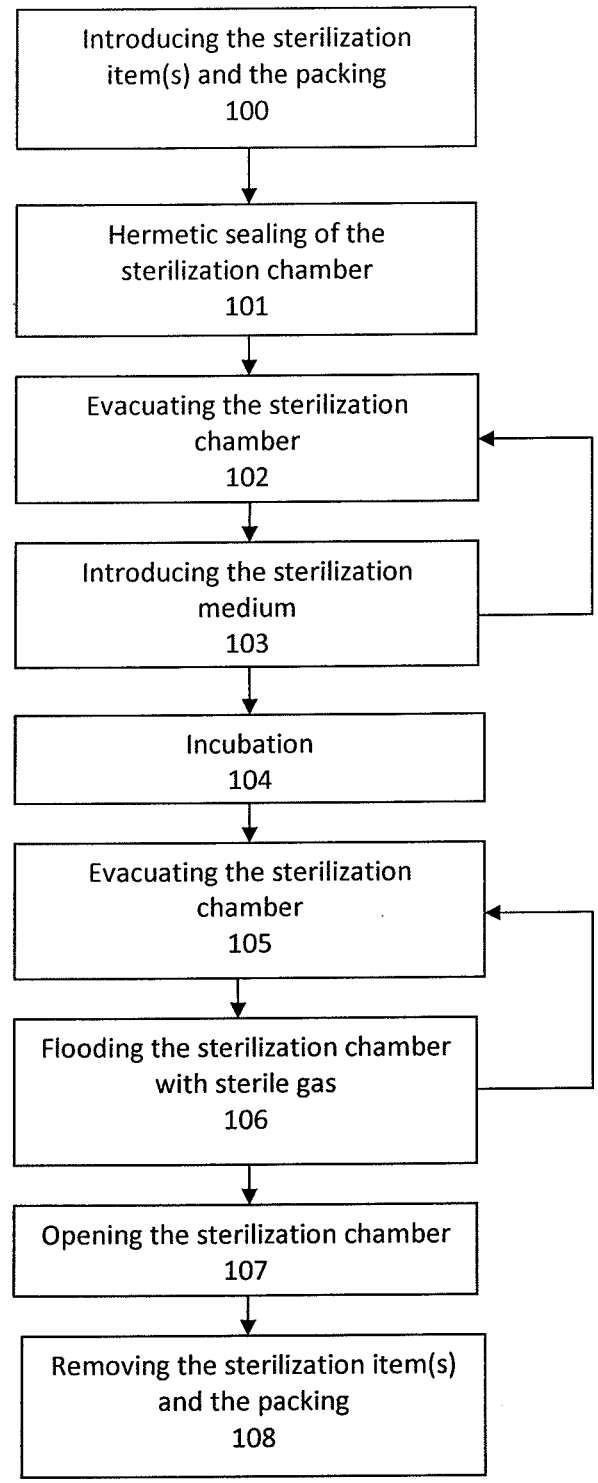
FIG. 1 shows the course of the process in the form of a flowchart.
Figure 2:
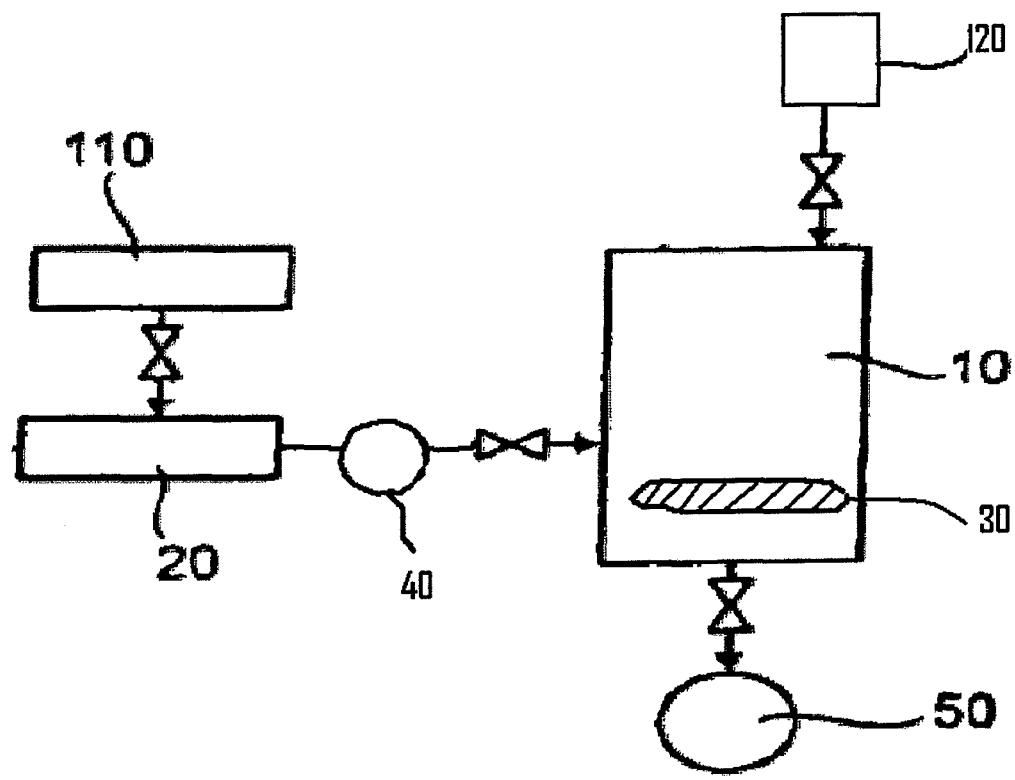
FIG. 2 shows a schematic view of an exemplary sterilization device.

FIG. 2 shows a device according to the invention for sterilization. A packing 30 the volume of which can expand greatly during the evacuation steps 102 and 105 is situated in the sterilization chamber 10. The evacuation takes place via a vacuum pump 50 which is connected to the sterilization chamber. In addition a means for supplying a sterilization medium 20 is connected to the sterilization chamber 10. The sterilization medium may be introduced from this vessel 20 through a pump 40 into the sterilization chamber, but the sterilization medium may also be transferred to the sterilization chamber through the vacuum pump 50. The sterilization medium may be supplied into the vessel 20 from a means for generating this sterilization medium 110. This may be a steam generator or an ozone generator, for example. In addition, the sterilization chamber 10 has a line to a source for a sterile gas 120.

Figure 3:
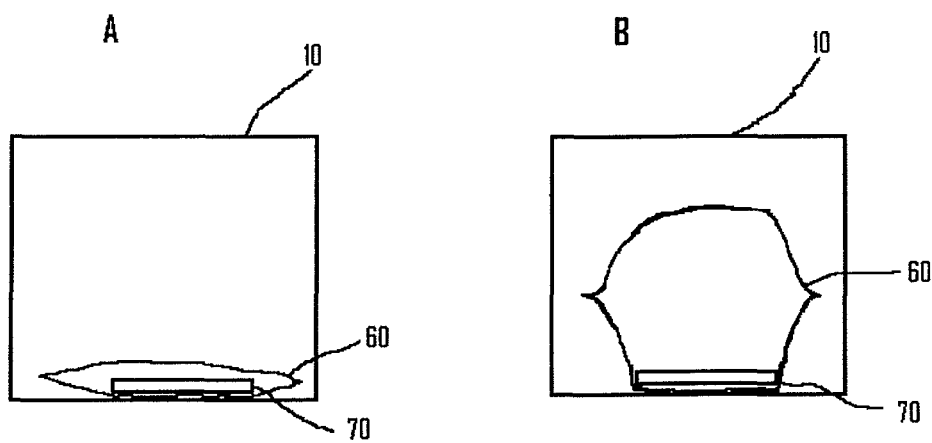
FIG. 3 shows schematically the sterilization chamber of a sterilization device according to the prior art with sterilization item(s) in an outer packaging in a vented condition (A) and in an evacuated condition (B).

FIG. 3 shows a sterilization chamber 10 with sterilization item(s) 70 according to the prior art. The sterilization item(s) 70 is in an outer packaging. FIG. 3A shows the sterilization chamber 10 in the evacuation or vacuum phase. The outer packaging here is inflated to the maximum volume of the packaging.

Figure 4:
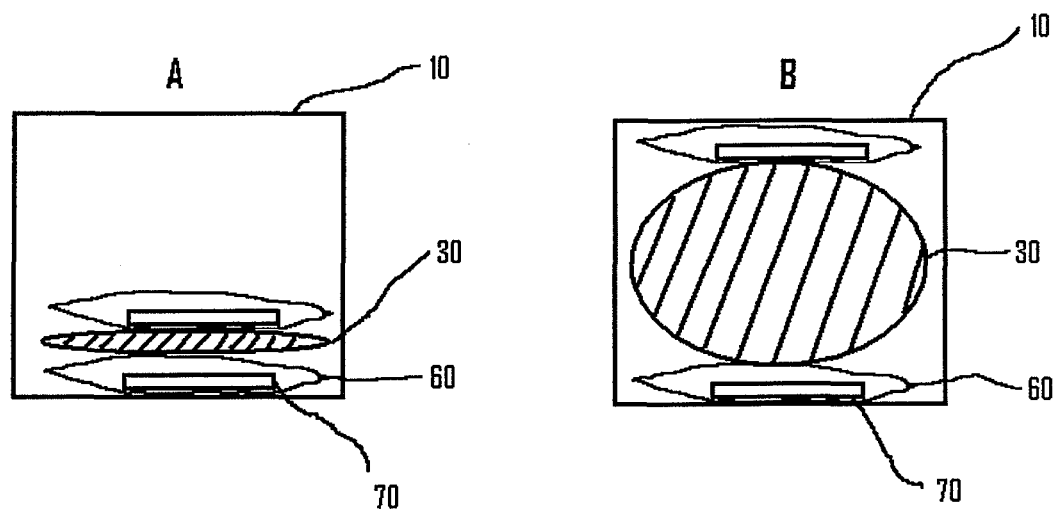
FIG. 4 shows schematically an embodiment of a sterilization chamber of a sterilization device according to the invention with sterilization item(s) in an outer packaging in the vented state (A) and in the evacuated state (B).

FIG. 4 shows a detail of a sterilization device according to the invention. A packing 30 embodied as a plastic bag is arranged between two outer packagings with sterilization item(s) 70 in the sterilization chamber 10. In FIG. 4A, the sterilization chamber 10 is shown at ambient pressure or in the phase with loading with sterilization medium. FIG. 4B shows the sterilization chamber 10 in the evacuation or vacuum phase. In contrast with the prior art, the plastic bag 30 here has been inflated up to its maximum volume. The dimensions in the sterilization chamber 10 are selected so that expansion of the outer packaging around the sterilization item(s) is prevented due to the space required by the plastic bag 30 in the evacuation phase. In contrast with the plastic bag 30, the outer packaging is gas-permeable, so that the air is forced out of the packaging by the plastic bag 30. Since the spatial displacement of the plastic bag is much lower at ambient pressure, the plastic bag and the sterilization item(s) may easily be inserted into and removed from the sterilization chamber.

Due to the method according to the invention and the device according to the invention, the number of required vacuum-pressure cycles can be reduced. A shortening of the sterilization time, savings of sterilization medium and energy can thereby be achieved.

The invention claimed is:

1. A method for sterilizing sterilization items in an evacuable sterilization chamber, characterized by the following method steps:
   a) introducing at least one sterilization item and at least one packing into the evacuable sterilization chamber, characterized in that the packing is a flexible sealed gas-containing, gas-impermeable hollow body,
   b) hermetically sealing the sterilization chamber,
   c) evacuating the sterilization chamber and thereby lowering the pressure,
   d) introducing a sterilization medium into the sterilization chamber and thereby raising the pressure,
   e) repeating steps c) through d) at least once,
   f) leaving the sterilization medium in the sterilization chamber for a predetermined period of time to achieve a predetermined level of disinfection,
   g) evacuating the sterilization chamber,
   h) flooding the sterilization chamber with a sterile gas,
   i) repeating steps g) through h) as needed to remove the sterilization medium from the sterilization chamber and the sterilization item,
   j) opening the sterilization chamber,
   k) removing the sterilization item and the packing from the sterilization chamber.

2. The method according to claim 1, characterized in that the pressure is lowered to less than 110 mbar abs. in step c).

3. The method according to claim 1, characterized in that the pressure is raised to more than 2 bar abs. in step d).

4. The method according to claim 1, characterized in that the hollow body is a plastic bag.

5. The method according to claim 1, characterized in that the sterilization item is in a gas-permeable outer packaging.

6. The method according to claim 5, characterized in that the gas-permeable outer packaging is flexible.

7. The method according to claim 1, characterized in that the sterilization item has air-filled hollow spaces that are open to the environment.

8. The method according to claim 5, characterized in that the sterilization item is a tubing system.

9. The method according to claim 5, characterized in that the sterilization item is a cassette system.

10. The method according to claim 1 using a sterilization device comprising the evacuable sterilization chamber having the at least one packing, a vacuum generator, means for supplying a sterilization medium, and a control unit or regulating unit for performing the method.

* * * * *